United States Patent [19]

Rabinowitz et al.

[11] Patent Number: 4,856,514

[45] Date of Patent: Aug. 15, 1989

[54] CONTROL APPARATUS FOR A LIGHTED, HAND HELD, SURGICAL ELECTRODE HOLDER

[75] Inventors: Dan Rabinowitz, Chicago; John Saeli, Wheaton, both of Ill.

[73] Assignee: Medi-Tech, Inc., Chicago, Ill.

[21] Appl. No.: 77,103

[22] Filed: Jul. 23, 1987

[51] Int. Cl.⁴ .............................................. A61B 17/39
[52] U.S. Cl. .......................... 128/303.14; 128/303.17; 128/23
[58] Field of Search ................ 128/23, 303.13–303.19; 219/230; 362/119, 120, 804

[56] References Cited

U.S. PATENT DOCUMENTS

| | | | |
|---|---|---|---|
| 2,200,322 | 5/1940 | Amesen | 128/303.14 |
| 4,012,686 | 3/1977 | Heme | 128/23 X |
| 4,071,028 | 1/1978 | Perkins | 128/303.14 |
| 4,463,759 | 8/1984 | Garito et al. | 128/303.17 |
| 4,688,569 | 8/1987 | Rabmowitz | 128/303.14 |

FOREIGN PATENT DOCUMENTS

| | | | |
|---|---|---|---|
| 179607 | 9/1954 | Fed. Rep. of Germany | 128/303.17 |
| 365994 | 1/1973 | U.S.S.R. | 128/303.17 |
| 515956 | 12/1939 | United Kingdom | 128/303.17 |

*Primary Examiner*—Lee S. Cohen
*Attorney, Agent, or Firm*—Joseph Clark MacKenzie

[57] ABSTRACT

A control apparatus for use in conjunction with a lighted, hand held, surgical electrode holder and any electrosurgical current generator normally intended to function with a non-lighted, hand held surgical electrode holder, that permits delivery of illuminating current to the lighted holder's lamp, while simultaneously permitting on a selective basis, cutting current or coagulation current to pass through the holder's active electrode. In addition, the control apparatus provides the lamp with a delay shut-off which thereby permits a surgeon to inspect the site of surgery, either before or following surgery, when cutting or coagulation current does not flow.

12 Claims, 2 Drawing Sheets

CONTROL APPARATUS FOR A LIGHTED, HAND HELD, SURGICAL ELECTRODE HOLDER

BACKGROUND

Electrosurgery is a form of surgery in which living body tissue is removed or destroyed by heat generated by an alternating high frequency current. A variety of systems for supplying the current have been developed. Most of them utilize an active and an indifferent electrode. The indifferent electrode is often a large metal plate which is placed on the leg, arm or back of the patient.

The high frequency current radiates through the tissues from the site of tissue contact of the small active electrode toward the larger indifferent electrode, then back to a power oscillator of an electrosurgical unit (ESU), and back again to the site of tissue contact of the small electrode, in a continuing radiating cycle. In this manner, the current is not evenly dispersed but instead attains a density or concentration at the site of the small electrode tissue contact that is great enough to produce cellular destruction, known as electrosurgery.

The active electrode may have a wide variety of shapes such as a needle or blade for cutting, or a wire loop for scraping.

When touched by the active electrode, tissue is disintegrated, but the heat generated does not penetrate the body deeply. Thus, the active electrode acts as a scalpel with the advantage that in the process of cutting, small blood vessels are sealed by the heat thereby reducing bleeding.

A number of electrosurgical instruments have been developed and used wherein an active electrode is attached to an insulated handle and a high frequency current is applied thereto from an electrosurgical current generator. Electrosurgical instruments found to be particularly safe and effective for surgical applications are those which incorporate finger actuated switches, those which allow for readily interchangeable electrodes, those which are water resistant, and those which are thin and properly balanced for close surgical use where a certain "feel" is necessary for the surgeon to properly use the instrument. An instrument such as the aforedescribed one is commonly referred to as an "electrosurgical pencil", particularly in view of its slenderness, and shape which resembles a pencil. Other names by which such an instrument is known include "hand held electrode holder" or "hand held, electrosurgical electrode holder", or "finger actuated electrosurgical electrode holder". Examples of finger actuated, electrosurgical electrode holders are described in United States Letters Patent Nos. 4,034,761 or 3,801,766 or 4,112,950 or 4,170,234.

A variation of such an instrument is one which is actuated by a foot controller rather than finger actuated switches. This latter variation is often referred to as a "foot actuated, electrosurgical electrode holder".

A more recent development in hand held, surgical electrode holders as described in copending U.S. Application Serial No. 872,166, filed 06/09/86 now U.S. Patent No. 4,688,569, issued Aug. 7, 1984, is that of a finger actuated electrosurgical electrode holder incorporating a light source such as a lamp for the purpose of illuminating the region of surgery. Such illumination is provided by means of an elongated fiber optic photoconductive device which extends generally longitudinally within the holder's active electrode, and which communicates in the holder with a light source such as a lamp.

From the teachings of U.S. Application Serial No. 872,166 one can readily appreciate how a similar light illuminating means can be incorporated into a foot actuated electrosurgical electrode holder as opposed to a finger actuated electrosurgical electrode holder.

Whether the instrument is actuated by finger switches or by foot control switches, if it incorporates a lamp means to provide localized illumination to the region of surgery, it can be referred to as a "lighted, hand held, electrosurgical electrode holder".

One object of this invention is to provide an adapter than can electrically connect to the lighted, hand held, electrosurgical electrode holder, and also to an ESU that is normally compatible with a non-lighted hand held electrosurgical electrode holder, and which can enable the electrosurgical current generator to light the lamp in the holder while at the same time permitting current for cutting (cut current) or current for coagulating (coag current) to pass through the holder's active electrode. That is, it is an object of the invention to provide a lighted, hand held, electrosurgical electrode holder which can also exactly duplicate any hand held, non-lighted surgical electrode holder.

Another object of this invention is to provide a means for delaying lamp shut-off, in order to enable the surgeon to inspect his region of surgery either prior to or following surgery.

Another object of this invention is to provide a means of insulating a hand held electrosurgical electrode holder from 60 $H_z$ leakage current.

Another object of this invention is to provide a means of isolating the active electrode in the holder from its switches, thereby permitting low voltage, low current, low cost, small switches to be used.

The foregoing and the objectives, features and advantages will be more apparent in view of the following detailed description of exemplary preferred embodiments, when taken in conjunction with the accompanying drawings.

DRAWINGS

DESCRIPTION OF THE PREFERRED EMBODIMENTS

Figure 1:
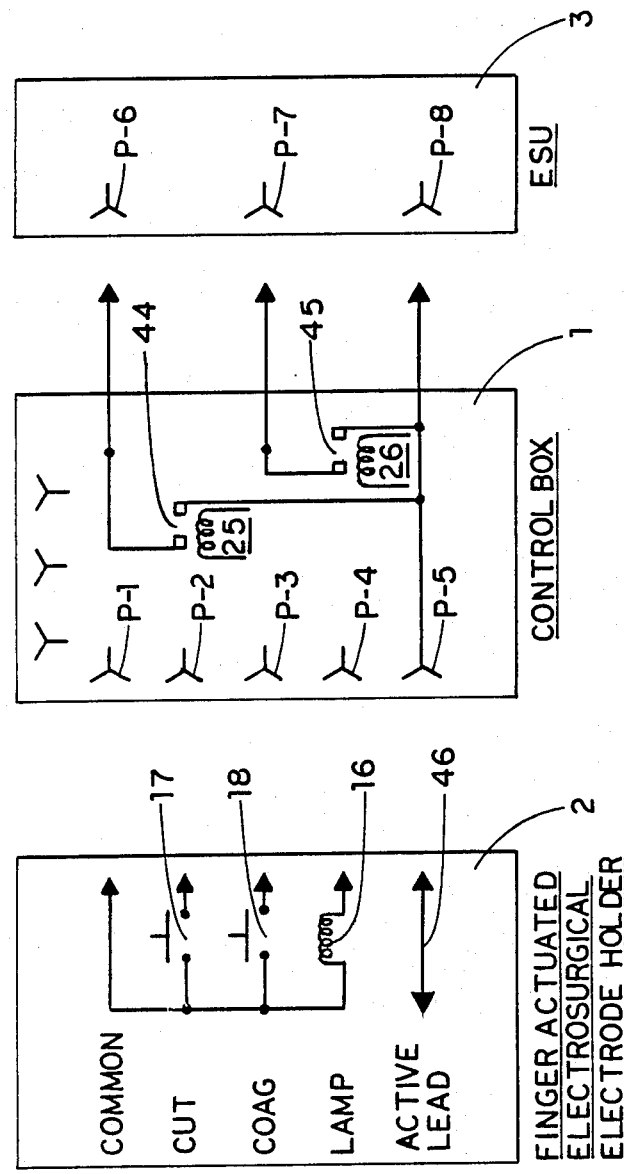
FIG. 1 is a functional diagram showing the interconnection between the control apparatus according to the invention, a lighted hand held surgical electrode holder, and an electrosurgical current generator.

Referring now to the drawings, FIG. 1 shows the electrical interconnection between the control apparatus or box 1 according to the invention, a hand held electrode holder 2, and an electrosurgical current generator ESU 3. Hand held surgical electrode holder 2 incorporates a lamp 16, an active electrode 46, a CUT switch 17 for selectively providing cutting current from the electrosurgical current generator 3 to active electrode 46, and a COAG switch 18 for selectively providing coagulation current from the electrosurgical current generator 3 to active electrode 46.

The control apparatus incorporates a pair of relay contacts 44 which close upon actuation of CUT switch 17, and a pair of relay contacts 45 which close when COAG switch 18 is actuated. Such contacts may be provided by either mechanical or electro-optical devices.

Box 1, holder 2, and generator 3 are coupled together, as by cables terminating in plugs, as indicated by the reference characters P-1 through 8, the box 1 also being similarly coupled to the AC line, as indicated by the reference characters P-9, P-10 and P-11.

Figure 2:
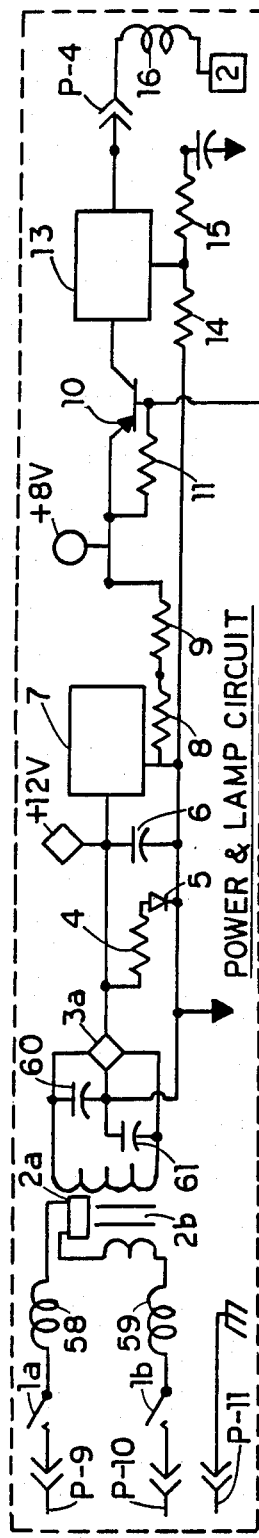
FIG. 2 is a schematic representation of details of the control circuits of FIG. 1.
Figure 2:
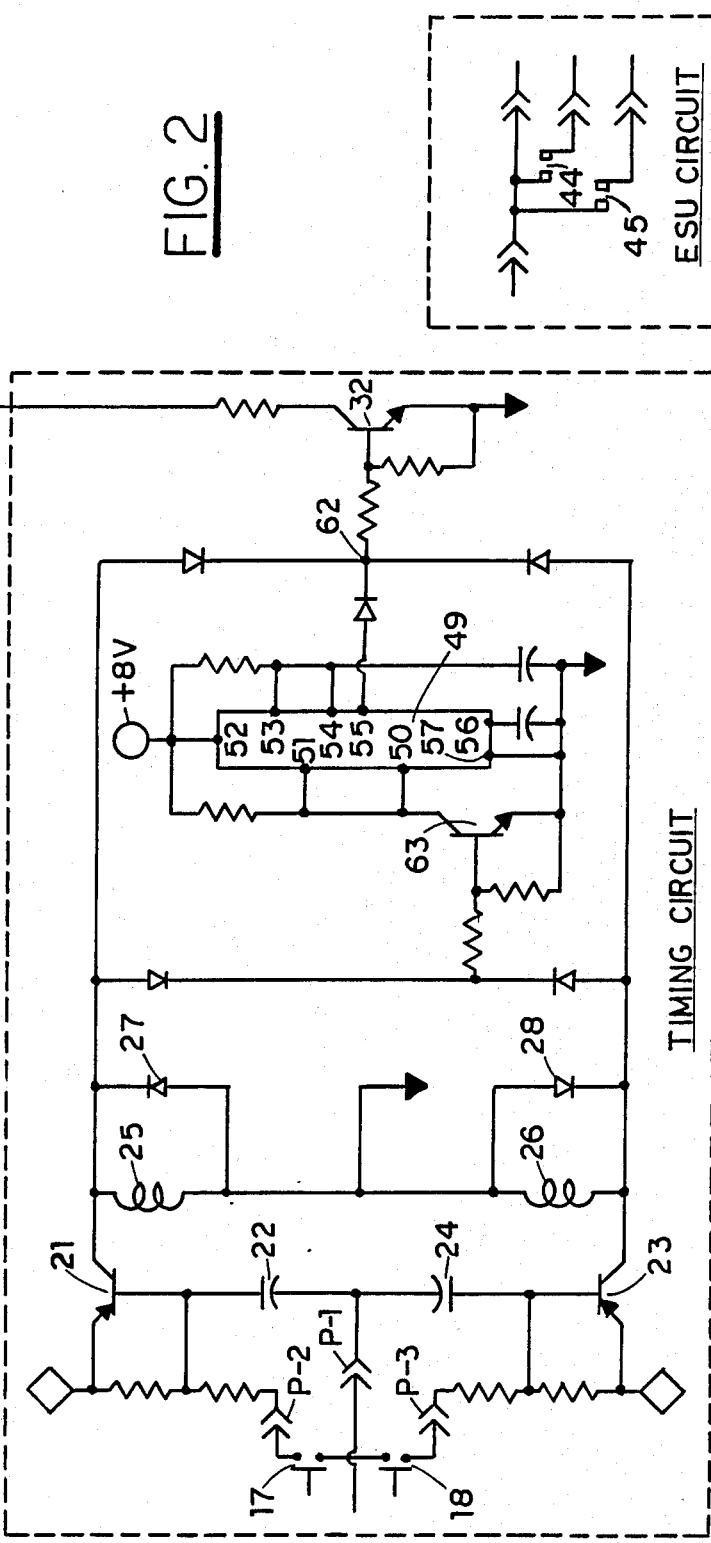

Referring now to FIG. 2, the circuitry contained within the dashed-line enclosure is housed within the control box 1, which may also include other elements (not shown) which are not essentials of the present invention. To begin with, a power and lamp circuit has a pair switches 1a and 1b which are the power or on-off switches used to provide line voltage to the control box. A transformer 2b, protected by a thermal protector 2a, is a step-down transformer which provides a low voltage AC to a rectifier bridge 3a at the required value for a regulator 7.

Rectifier bridge 3a converts the voltage from AC to DC. A light emitting diode 5 in series with resistor 4 provides a light which visibly indicates when power switches 1a and 1b are engerized (turned on). Audible indicating means might also be used for this purpose.

A capacitor 6 provides a ripple filter for voltage from rectifier bridge 3a. Voltage regulator 7 in combination with a pair of resistors 8 and 9 supplies regulated voltage to a timer 49 and to a lamp power supply transistor 10 and a regulator 13.

Transistor 10 in combination with a resistor 11 acts as a switch for lamp 16. When transistor 10 is turned on, regulator 13, in combination with a pair of resistors 14 and 15, reduces the regulator 7 voltage to the required lamp voltage.

Transistor 10 is turned on when a transistor 32 is turned on, and transistor 32 is turned on when either CUT switch 17 or COAG switch 18 is energized (closed).

Also, a timing circuit in box 1 provides for controlling transistor 32 when the timer 49 of said circuit is activated. Timer 49 is conventional and may provide either a fixed or adjustable timing action in the form of a counting cycle which begins when switch 17 or 18 opens, during which cycle the terminal 55 provides a voltage for turning transistor 32 on.

When the CUT switch 17 or COAG switch 18 closes, the corresponding one of a pair of transistors 21 and 23 turns on, thereby letting current pass through to energize a relay 25, or a relay 26 respectively which, in turn, causes either switch 44 or 45 in the ESU circuit to close. Because cutting and coagulating current is actually switched in the control box 1, the active electrode is therefore isolated from switches 17 and 18, which therefor may be low voltage, low current, low cost, small switches, despite their proximity in the holder to the active electrode and lead 46.

A pair of capacitors 22 and 24 prevent RF current from turning "on" transistor 21 or 23.

A pair of flywheel diodes 27 and 28 filter out voltage spikes when CUT switch 17 or COAG switch 18 open and when relay 25 or 26 de-energizes.

On timer 49, terminal 50 is an inhibit terminal and terminal 51 is a reset terminal.

When either CUT switch 17 or COAG switch 18 is closed, relay 25 or 26 are energized which, in turn, energize ESU contacts 44 or 45. Furthermore, via transistor 63, the timer is reset thru terminal 51 and a new timing cycle in inhibited thru terminal 50. Furthermore, 8 volts appears at diode junction 62 which turns on transistors 32 and 10 allowing current to reach lamp 16.

When either CUT switch 17 or COAG switch 18 are turned off or deactivated, relay 25 or 26 turns off and both switches 44 and 45 become open. Furthermore, the inhibit terminal of the timer is turned off and timer begins counting. In the meantime the lamp light stays on because there will be 8 volts at the junction 62 while the counting cycle lasts.

When the predetermined counting cycle ends, the voltage at terminal 55 of the timer 49 goes to zero which causes both transistors 32 and 10 to de-energize, thereby causing lamp 16 to shut off until such time as switch 17 or 18 is activated.

A pair of coils 58 and 59 in primary side of the power and lamp circuit decouple RF on the active conductor from the line. A pair of capacitors 60 and 61 bypass the RF around the rectifier bridge. That is to say, that, except for active lead 46, the holder and circuitry therein is isolated from RF cutting or coagulation current from the generator 3. Such isolation prevents loss of cutting or coagulation power which would occur, were RF allowed to get into the power and lamps circuitry or into the AC line which energizes that circuitry.

To increase the life of the lamp, an RC circuit could be added to the lamp power control circuit to provide a soft or gradual turn-on of the lamp.

What is claimed is:

1. In electrosurgical apparatus having a hand held electrode holder for a surgical electrode therein, and including an electrosurgical current generator having output terminals for supplying current to said electrode, said electrosurgical apparatus also having control apparatus with means for operating said surgical electrode, said electrode holder also having a lamp for illuminating the region of surgery, the combination comprising:

a housing;

lamp circuit means in said housing for providing current to said lamp;

switching means in said holder for selectively causing current of said electrosurgical current generator to be delivered by connecting means, or to cease being delivered thereby, to the said holder's electrode for cutting or for coagulation;

first connecting means associated with said housing and electrically connecting said control apparatus to output terminals of said electrosurgical current generator;

second connecting means associated with said housing and electrically connecting the said control apparatus to input terminals of the said electrode holder;

electrode isolating means for isolating the said electrode's switching means from its cut and coagulation current, whereby economical low current, low voltage switching means can be used;

holder isolating means for electrically isolating the said lamp circuit means and said second connecting means from radio frequency currents, whereby performance of the said lamp is not impaired, and whereby there is virtually no reduction in cut or coagulation power due to diversion of radio frequency current from said electrode.

2. The invention of claim 1 further including delay shut-off means for providing predetermined time delay shut-off to said lamp, whereby the user of said hand held surgical electrode holder will be able to inspect his site of operation, either before or following surgery, without the flow of high frequency current to the said electrode; said delay shut-off means being responsive to said switching means ceasing to cause current to be delivered to said electrode.

3. The invention of claim 1 wherein said lamp circuit means includes means for isolating the said hand held surgical electrode holder from 60 $H_z$ current leakage.

4. A control apparatus that enables a hand held surgical electrode holder with lamp means for illuminating the region of surgery to operably interconnect with any electrosurgical current generator that has control output terminals for electrically connecting to hand held electrosurgical electrode holders that do not contain said lamp means, said control apparatus comprising:
   a power and lamp circuit incorporating means for delivering appropriate voltage to said lamp means upon energization of either a cutting switch or a coagulation switch of said hand held electrosurgical electrode holder;
   a timing circuit incorporating timing means for providing a predetermined shut-off delay to said lamp means; and
   an ESU circuit having means for delivering cutting current from said electrosurgical current generator to an electrode in said holder upon actuation of said cutting switch, and said ESU circuit also having means for delivering said coagulation current to said electrode upon actuation of said coagulation switch.

5. A control apparatus as defined in claim 4 wherein said power and lamp circuit comprises a step down transformer, a voltage regulator, and transistor means to provide appropriate voltage to said lamp means.

6. A control apparatus as defined in claim 4 wherein said timing circuit comprises:
   cutting current switching means and coagulation current switching means responsive to actuation of said cutting switch and said coagulation switch respectively for delivering current to said electrode;
   said timing means being constructed and arranged to begin its counting cycle upon deactuation of said cutting current switching means, or upon deactuation of said coagulation switching means, for de-energizing the said lamp means at the end of said counting cycle.

7. A control apparatus as defined in claim 4 wherein said ESU circuit is isolated from the timing circuit by relay means in said control apparatus for controlling cutting current and coagulating current in response to actuation of said cutting switch and coagulating switch respectively.

8. An electrode circuit for a finger actuated or foot actuated hand held surgical electrode holder having electrical circuitry including cut and coagulation current switching means and a lamp for providing illumination to the region of surgery comprising:
   means for electrically interconnecting said electrical circuitry of the said holder and an electrosurgery high frequency current generator that provides cut and coagulating currents to an active electrode in said holder;
   means for providing a predetermined time delay shut-off to the said lamp;
   means for providing a predetermined level of lamp illumination;
   means for isolating said active electrode in the said holder from said cut and coagulation switching means;
   means for isolating the said holder from radio frequency currents, while otherwise allowing such currents to pass through said holder to said electrode.

9. In combination, an active electrosurgical electrode holder means, a control apparatus, and cable means for connecting said holder means with said apparatus;
   said cable means having an electrical conductor therein extending at one end to said apparatus and at another end to said holder means, said holder means being constructed and arranged for electrically connecting the latter said end to an active electrosurgical electrode in said holder means, and said holder means having first switching means therein operable by an operator for electrically connecting and disconnecting the RF output of an electrosurgical generator to and from, respectively, said one end;
   said control apparatus having second switching means therein operable by said first switching means for causing saidd second switching means to connect and disconnect, at the will of the operator, said RF output to and from, respectively, said one end, said first and second switching means being constructed and arranged such as to be electrically isolated, one from the other, in respect of said RF output;
   said second switching means having means for connecting it to said generator for receiving therefrom the said RF output.

10. The invention of claim 1, said holder means having electrically-energized illuminating means, and said control apparatus having means therein for electrical energization of said illumination means in response to said first switching means being operated such as to cause said second switching means to connect said RF output to said one end of said cable means.

11. In combination, an active electrosurgical electrode holder means, a control apparatus, and cable means for connecting said holder means with said apparatus;
   said cable means having an electrical conductor therein extending at one end to said apparatus and at another end to said holder means, said holder means being constructed and arranged for electrically connecting the latter said end to an active electrosurgical electrode in said holder means, and at least one of said holder means and said control apparatus having switching means therein operable by an operator for effectively electrically connecting and disconnecting the RF output of an electrosurgical generator to and from, respectively, said one end;
   said holder means having electrically-energized illuminating means, and said control apparatus having time delay means therein for controlling electrical energization of said illuminating means;
   said time delay means being responsive to disconnection, from said one end of said RF output by operation of said switching means, for causing said illuminating means to remain illuminated for a predetermined time, at the end of which said time delay means causes said illumination to cease until said switching means is next operated for connecting said RF output to said one end;

said illuminating means becoming electrically-energized in response to operation of said switching means for connecting said RF output to said one end.

12. The invention of claim 11, including further switching means in said control apparatus;
said further switching means being operable by the first said switching means for causing said further switching means to connect and disconnect, at the will of the operator, said RF output to and from, respectively, said one end, said first said and said further switching means being constructed and arranged such as to be electrically isolated, one from the other, in respect of said RF output.

* * * * *